United States Patent [19]

Sagane

[11] 3,975,287

[45] Aug. 17, 1976

[54] LIQUID CRYSTAL COMPOSITION FOR ELECTRIC FIELD INDICATION

[75] Inventor: Masahiko Sagane, Hiratsuka, Japan

[73] Assignee: Kansai Paint Company, Ltd., Amagasaki, Japan

[22] Filed: Oct. 22, 1974

[21] Appl. No.: 516,986

Related U.S. Application Data

[62] Division of Ser. No. 331,692, Feb. 12, 1973, Pat. No. 3,867,016.

[30] Foreign Application Priority Data

Feb. 17, 1972  Japan.................................47-16037

[52] U.S. Cl............................. 252/299; 23/230 LC; 252/408; 350/160 LC
[51] Int. Cl.$^2$........................ C09K 3/34; G02F 1/13
[58] Field of Search...................... 252/408 LC, 299; 23/230 LC; 350/160 LC; 428/1

[56] References Cited
UNITED STATES PATENTS

| | | | |
|---|---|---|---|
| 3,627,408 | 12/1971 | Fergason............................. | 252/299 |
| 3,656,909 | 4/1972 | Dixon............................. | 23/230 LC |
| 3,744,920 | 7/1973 | Adams et al.................. | 350/160 LC |
| 3,867,016 | 2/1975 | Sagane.............................. | 252/299 |

*Primary Examiner*—Benjamin R. Padgett
*Assistant Examiner*—T. S. Gron
*Attorney, Agent, or Firm*—Wigman & Cohen

[57] ABSTRACT

A liquid crystal composition for indicating the occurence of an electric field which has a long effective life, assumes a clear color change and comprises from about 10 to about 60 % by weight of a cholesteryl carbamate having, as the substituent group at the nitrogen atom of the carbamate, an aliphatic hydrocarbon group, a monocyclic aromatic hydrocarbon group or a substituted hydrocarbon group, and from about 40 to about 90 % by weight of a liquid crystal component compatible with the carbamate comprising cholesteric liquid crystal substances other than the cholesteryl carbamate.

13 Claims, No Drawings

LIQUID CRYSTAL COMPOSITION FOR ELECTRIC FIELD INDICATION

This is a divisional application of co-pending application Ser. No. 331,692, filed Feb. 12, 1973, entitled LIQUID CRYSTAL COMPOSITION FOR ELECTRIC FIELD INDICATION, in the name of Masahiko Sagane, the effective filing date of said co-pending application being claimed herein, now U.S. Pat. No. 3,867,016.

This invention relates to a liquid crystal composition containing cholesteric liquid crystal substance which is used for indicating the occurence of an electric field. Further, this invention relates to a novel liquid crystal composition which has a long effective life for indicating the occurence of the electric field. Still further, this invention relates to a novel liquid crystal composition which assumes a clear color change in indicating the occurence of electric field. More particularly, the invention relates to a liquid crystal composition which comprises from about 10 to about 60% by weight of a cholesteryl carbamate having, as the substituent group at nitrogen atom of the carbamate, an aliphatic hydrocarbon group, a monocyclic aromatic hydrocarbon group or a substituted hydrocarbon group, and from about 40 to about 90% by weight of a liquid crystal component compatible with the carbamate comprising cholesteric liquid crystal substances other than the cholesteryl carbamate.

In the conventional art, only the substances showing the nematic state have been used as the liquid crystal substances fo the purpose of indicating the electric field, while the cholesteric liquid crystal substances have been used for the indication of temperatures, the latter have never been used for the indication of the electric field. This is owing to the fact that the effective life of the cholesteric liquid crystal substance is very short when it is used for the indication of the electric field. In other words, the cholesteric liquid crystal substance rapidly loses its ability for indicating the electric field. Though it can be temporarily recovered by imparting shear stress, such recovery becomes impossible after being in use for several hundred hours.

Being different from the conventionally known cholesteric liquid crystal substances, the liquid crystal composition of the present invention has made great strides in the life of response to the occurence of the electric field. In addition to that, the composition of the invention indicates the occurence of the electric field with color changes, while the known nematic liquid crystal substances indicate it mainly with the phenomenon of becoming turbid. Accordingly, the composition of the present invention offers excellent indicating and esthetic effects in use.

The composition of the present invention is characterized in the use of cholesteryl carbamates having substituent groups at their nitrogen atoms.

The cholesteryl carbamates which have aliphatic hydrocarbon groups having a carbon atom number of not more than 5 have been well known, however, such cholesteryl carbamates have not been considered liquid crystal substances, and of course they have not been used for the indication of the electric field. The carbamate portions (urethane bonds) of such cholesteryl carbamates have a cohesive property which differs from other cholesteryl derivatives and hinders the molecular orientation of the cholesteric liquid crystal phase. This is the reason for overlooking the liquid crystal properties of the cholesteryl carbamates.

The inventor of the present invention has found that some cholesteryl carbamates exhibit the properties of the cholesteric liquid crystal substances, when admixed with a liquid crystal component. It is believed that the cohesive property of the cholesteryl carbamates that is too intense to show the property of cholesteric liquid crystal substance which is weakened by the effect of dilution with liquid crystal component.

As the result of extensive studies with regard to the cholesteryl carbamates themselves and the compositions containing the cholesteryl carbamates, the present invention has been developed. The liquid crystal composition containing the cholesteryl carbamates have very long effective lives of response to the electric field. The reason for this is not clearly understood, however, it is believed that the cohesive power of the carbamate portion hinders the deterioration being caused by the permanent structural changes of the liquid crystal composition.

When the cholesteryl carbamate is employed with the liquid crystal resulting composition, the viscosity of the composition is markedly increased. The increase of viscosity is due to the fact that the dipole moment of the cholesteryl carbamate molecule is quite large owing to its polar group which lowers the rate of molecular transfer within the liquid crystal composition. This appears to be another reason why the liquid crystal composition containing a cholesteryl carbamate maintains its structure effectively.

The cholesteryl carbamates as used in the present invention are those in which one of two hydrogen atoms being combined to the nitrogen atom is substituted by a hydrocarbon group or substituted hydrocarbon group. The hydrocarbon group may be aliphatic or aromatic, however, the more the group is a linear type the more the group is prefered as the substituent of the cholesteryl carbamate because of the high crystallizing tendency. Where the hydrocarbon group is aliphatic, the group can contain a double bond or double bonds, the carbon atom number thereof should be not more than 24, and the substituent group of a linear chain structure or almost linear chain structure is preferable. The aliphatic hydrocarbon group is derived from the aliphatic hydrocarbon compound used for the preparation of the cholesteryl carbamate according to any of the methods described hereinbelow.

The preparation of the cholesteryl carbamate having the substituent group which is aliphatic or aromatic can be carried out by one or two different methods. One method is the reaction of a primary amine having an aliphatic hydrocarbon group, an aromatic hydrocarbon group or a substituted hydrocarbon group as a substituent with a cholesteryl chloroformate obtained from, for example, cholesterol and phosgene to cause dehydrochlorination condensation. Examples of such aliphatic, aromatic or substituted hydrocarbon groups contained in the primary amine are described hereinbelow.

As the aliphatic hydrocarbon groups a methyl group, ethyl group, n-propyl group, n-butyl group, n-pentyl group, n-hexyl group, n-heptyl group, n-octyl group, n-nonyl group, capryl group, n-undecyl group, lauryl group, myristyl group, palmityl group, stearyl group, arachidyl group, lignoceryl group, myristoleyl group, oleyl group, elaidyl group, erucyl group, tiglyl group and a linolyl group are prefered.

The prefered aromatic hydrocarbon group are monocyclic ones which include a phenyl group and those having an aliphatic hydrocarbon group having a carbon number of not more than 8 as a substituent in an alkaryl (alkyl aryl) from such as a p-tolyl group, p-ethyl phenyl group, p-n-butyl phenyl group, p-n-octyl phenyl group, and in an aralkyl (aryl alkyl) from such as a benzyl group, 2-phenyl ethyl group, 3-phenyl propyl group and a cinnamyl group.

As the substituted hydrocarbon group there are, for example, 2-(2-alkoxyethoxy) ethyl groups in which the "alkoxy" is alkoxy group having from 1 to 4 carbon atoms, for example, methoxy, ethoxy or n-butoxy, substituted phenyl groups having a substituent group other than hydrocarbon groups in its aromatic nucleus such as an anisyl group, phenetyl group, p-chlorophenyl group or p-nitrophenyl group and hydroxy-substituted aliphatic groups such as ricinoleyl group.

The second method of synthesis of the cholesteryl carbamates is such that a monoisocyanate compound having an aliphatic or an aromatic hydrocarbon group or the like as the substituent is caused to react with the terminal hydroxyl group of cholesterol to form a urethane linkage. Such isocyanate compounds are derived from the corresponding monocarboxylic acids having an aliphatic or an aromatic hydrocarbon group or the like exemplified for the first method of synthesis as above through the corresponding acid chlorides and acid azides by well known methods. In this manner of synthesis the substituent group introduced in the cholesteryl carbamate has a chemical formula such that one methylene group in the alpha position is diminished from the chemical formula for the hydrocarbon group in the corresponding monocarboxylic acid used as the starting material due to the dislocation of the alpha carbon atom.

The usual reaction conditions in the preparation of the known carbamates can be applied for both methods of synthesis, in which no difficulty is caused.

The content of the cholesteryl carbamate in the composition of the present invention is made within the range of about 10 to about 60 % by weight. If the content of cholesteryl carbamate is smaller than about 10 % by weight, the quite long effective life of response to an electric field can not be expected. If the content of cholesteryl carbamate exceeds about 60 % by weight, the composition does not show the property of a liquid crystal at room temperature, so that is not suitable for the indication of the electric field.

These cholesteryl carbamates can be used solely or in admixture for the cholesteryl carbamate component of the invention in which case a great variety of the indication effects may be obtained.

In order to impart the property of a liquid crystal to such cholesteryl carbamates for the indication of an electric field, it is necessary, as explained above, to dilute by admixing a liquid crystal component compatible with the carbamate. As for the component to be mixed, cholesteric liquid crystal substances besides the above cholesteryl carbamates are most suitable. By the addition of the cholesteryl carbamates to the liquid crystal component compatible with the carbamate comprising a cholesteric liquid crystal substance other than the carbamate there is obtained a longer effective life for indicating the electric field and different colors for indicating the electric field.

As the cholesteric liquid crystal substance for the above-mentioned liquid crystal component used, there are, for example, cholesteryl halides such as cholesteryl chloride and cholesteryl bromide, cholesteryl ethers such as cholesteryl methyl ether and cholesteryl ethyl ether, cholesteryl esters, cholesteryl carbonates, cholesteryl thiocarbonates, 24-methylcycloaltanol esters, 24, 28-dihydrocycloeucanol esters and cycloaltenol esters, and one or a mixture of two or more of them is used. It is preferable that the component of these substances, excluding the cholesteryl halides and cholesteryl ethers, in the component of cholesterol, cholesteryl carbonic acid, cholesteryl thiocarbonic acid, 24-methylcycloaltanol, 24,28-dihydrocycloeucanol and cycloaltenol, be an ester of those alcohol or carboxylic acid groups specified for the cholesteryl carbamates. That is, the substituent group is preferably an aliphatic hydrocarbon group having a carbon atom number of not more than 24, a monocyclic aromatic hydrocarbon group such as a phenyl group and so forth or a substituted hydrocarbon group such as 2-(2-methoxyethoxy)ethyl group and so forth.

The content of the liquid crystal component in the composition should be from about 40 to about 90% by weight. When the content of the liquid crystal component is below about 40% by weight, the composition does not show the property of the cholesteric liquid crystal because of the excessively eminent cohesion of the cholesteryl carbamates, and when the content exceeds about 90% by weight, the composition has no extended life effective for the indication for the electric field due to the dilution of the cholesteryl carbamates.

Further, if necessary, the liquid crystal component may contain a small amount of an organic solvent and/or a plasticizer as an additive. The additive having no liquid crystal property can only be used together with the cholesteric liquid crystal substances other than the cholesteryl carbamates aforementioned and the content of the additive may contain not more than about 10 % by weight of the composition because they have an acute lowering effect for the action of the cholesteryl carbamates.

In order that those skilled in the art may better understand the present invention and the manner in which it may be practiced, the following specific examples are given.

The additive having no liquid crystal properties can also be used in the liquid crystal component when moderate lowering of the viscosity of the composition for ease of treatment or adjustment of the hue is desired. For example, organic solvents such as benzene, toluene, xylene, methyl alcohol, ethyl alcohol, propyl alcohols, butyl alcohols, benzyl alcohol, acetone, methylethyl ketone, methyl-isobutyl ketone, cyclohexanone, isophorone, ethyl acetate, n-butyl acetate, ethyleneglycol monoethyl ether, ethyleneglycol monobutyl ether, ethyleneglycol monoethyl ether acetate, diethyleneglycol monoethyl ether, diethyleneglycol monoethyl ether acetate, diacetone alcohol, N, N-dimethyl formamide and N, N-dimethyl acetamide, and plasticizers such as di-n-butyl phthalate, di-n-octyl phthalate, di-2-ethylhexyl phthalate, dicyclohexyl phthalate, n-butyl benzyl phthalate and di-n-octyl sebacate can be used as the additive for the cholesteryl carbamate. N, N-dimethyl formamide and N, N-dimethyl acetamide have also the effect of extending the effective life of the liquid crystal composition.

EXAMPLE 1

Oleylamine (a commercial product of Kao Soap Co., Ltd., Japan trade name "Farmin O") and cholesteryl chloroformate in a molar ratio of 1 : 1 were subjected to dehydrochlorination condensation to obtain N-oleyl cholesteryl carbamate. Then a cholesteric liquid crystal composition consisting of 20% by weight of N-oleyl cholesteryl carbamate thus obtained, 50% by weight of oleyl cholesteryl carbonate and 30% by weight of cholesteryl chloride was prepared. This composition assuming a red color in room temperature was applied between the electroconductive surfaces of two sheets of conductive glass (NESA glass) to form a 50 microns layer. With a spacer, a liquid crystal cell having a sandwich structure was obtained.

When D.C. voltage of 220 volts was applied between the conductive surfaces of this cell, the layer of the liquid crystal composition was changed to green. The voltage was applied continuously, with some breaks for about 1500 hours. The intensity of the color was reduced only a slight degree in the initial stage and the color was stable thereafter. In order to test the starting response of the color change, the electric voltage was discontinued every 24 hours for several seconds, however particular deterioration was observed.

Shear stress was also applied to this liquid crystal composition, and just after the application of the shear stress, almost the same color change as that in the initial stage could be recovered.

To observe the color of liquid crystal layer, the cell was placed on a black plate, a white spotlight was applied to the layer from 60 degree slant direction, from the perpendicular direction, and the color was observed from the opposite 30° slant direction with the naked eye.

EXAMPLE 2

A clear green cholesteric liquid crystal composition was prepared by mixing 18% by weight of the N-oleyl cholesteryl carbamate as used in Example 1, 4% by weight of N-n-butyl cholesteryl carbamate obtained from n-butyl isocyanate and cholesterol, 55% by weight of oleyl cholesteryl carbonate and 23% by weight of cholesteryl chloride. An indicating cell for an electric field having a liquid crystal layer of 50 microns in thickness, which was similar to that of Example 1, was formed. The effective life of this cell for the response to a D.C. voltage of 220 volts was examined in like manner as the foregoing Example 1, and it was confirmed that the ability for indicating the electric field was maintained for at least 1500 hours.

In this Example, the color change of the liquid crystal composition in the indication of the electric field was from fresh green to dark green.

EXAMPLE 3

Oleic acid (A chemical reagent under Japanese Industrial Standard K-8218, class 1) was changed to acid chloride, and further changed to oleyl isocyanate through an acid azide. This isocyanate was reacted with cholesterol in a molar ratio of 1:1 to obtain N-substituted cholesteryl carbamate. A liquid crystal composition consisting of 50% by weight of the above cholesteryl carbamate and 50% by weight of cholesteryl chloride was prepared, and an indicating cell for an electric field was prepared in like manner as in Example 1. The effective response life to the electric field of this cell was tested by applying an A.C. voltage (50 Hz) of 250 volts. It was confirmed that this cell had a longer life than that in Example 1.

The color of this composition was red at room temperature in the absence of the electric voltage, and was green when the above-mentioned electric voltage was applied.

EXAMPLE 4

From the above disclosure and Examples, the advantages of the present invention may be fully understood. It should be emphasized, however, that the specific Examples described herein are intended as merely illustrative and in no way restrictive of the invention.

An indicating cell for an electric field was prepared in like manner as Example 1 using a liquid crystal composition consisting of 20% by weight of N-oleyl cholesteryl carbamate obtained in Example 1, 42% by weight of oleyl cholesteryl carbonate, 30% by weight of cholesteryl chloride and 8 % by weight of N, N-dimethyl formamide. The indicating cell was tested for the life for the response to the electric field applying the same condition as in Example 1 for about 1800 hours.

The indicating cell has shown no deterioration in coloring in continuous state and also in starting response.

What is claimed is:

1. A liquid crystal composition for indicating the occurrence of electric field which consists essentially of from 10 to about 60% by weight of a cholesteryl carbamate having as the substituent group at the nitrogen atom of the carbamate a member selected from the group consisting of a phenyl group and a monocyclic aromatic hydrocarbon group having a linear aliphatic hydrocarbon group of not more than 8 carbon atoms, and from about 40 to about 90% by weight of a cholesteric liquid crystal taken from the group consisting of cholesteryl halides, cholesteryl ethers, cholesteryl esters, cholesteryl carbonates, cholesteryl thiocarbonates, 24-methylcycloaltanol esters, 24, 28-dihydrocycloeucanol esters and cycloaltenol esters and mixtures thereof.

2. A liquid crystal composition as claimed in claim 1, in which said monocyclic aromatic hydrocarbon group having a linear aliphatic hydrocarbon group of not more than 8 carbon atoms is a member selected from the group consisting of a p-tolyl group, p-ethyl phenyl group, p-n-butyl phenyl group, p-n-octyl phenyl group, benzyl group, 2-phenyl ethyl group, 3-phenyl propyl group and a cinnamyl group.

3. A liquid crystal composition as claimed in claim 1, in which said cholesteryl esters, cholesteryl carbonates, cholesteryl thiocarbonates, 24-methylcycloaltanol esters, 24,28-dihydrocycloeucanol esters and cycloaltenol esters are esters of radicals selected from the group consisting of aliphatic hydrocarbon groups having a carbon atom number of not more than 24, monocyclic aromatic hydrocarbon groups and substituted hydrocarbon groups.

4. A liquid crystal composition as claimed in claim 3, in which said radicals are aliphatic hydrocarbon groups selected from a group consisting of a methyl group, ethyl group, n-propyl group, n-butyl group, n-pentyl group, n-hexyl group, n-heptyl group, n-octyl group, n-nonyl group, group, n-undecyl group, lauryl group, myristyl group, palmityl group, stearyl group, arachidyl group, lignoceryl group, myristoleyl group, oleyl group, elaidyl group, erucyl group, linolyl group and a tiglyl group.

5. A liquid crystal composition as claimed in claim 1, in which said radicals are monocyclic aromatic hydrocarbon groups selected from a group consisting of a phenyl group, p-tolyl group, p-ethyl phenyl group, p-n-butyl phenyl group, p-n-octyl phenyl group, benzyl group, 2-phenyl ethyl group, 3-phenyl propyl group and a cinnamyl group.

6. A liquid crystal composition as claimed in claim 1, in which said liquid crystal component further contains not more than about 10% by weight of organic solvent or plasticizer.

7. A liquid crystal composition as claimed in claim 6, in which said organic solvent is a member selected from a group consisting of benzene, toluene, xylene, methyl alcohol, ethyl alcohol, propyl alcohols, butyl alcohols, benzyl alcohol, acetone, methylethyl ketone, methylisobutyl ketone, cyclohexanone, isophorone, ethyl acetate, n-butyl acetate, ethyleneglycol monoethyl ether, ethyleneglycol monobutyl ether, ethyleneglycol monoethyl ether acetate, diethyleneglycol monoethyl ether, diethyleneglycol monoethyl ether acetate, diacetone alcohol, N,N-dimethyl formamide and N,N-dimethyl acetamide.

8. A liquid crystal composition as claimed in claim 6, in which said plasticizer is a member selected from a group consisting of di-n-butyl phthalate, di-n-octyl phthalate, di-2-ethylhexyl phthalate, dicyclohexyl phthalate, n-butyl benzyl phthalate and di-n-octyl sebacate.

9. A liquid crystal composition as recited in claim 1 wherein said cholesteryl halides are cholesteryl chloride and cholesteryl bromide.

10. A liquid crystal composition as recited in claim 1, wherein said cholesteryl ethers are cholesteryl methylether and cholesteryl ethylether.

11. A liquid crystal composition for indicating the occurrence of an electric field which consists essentially of from about 10 to about 60% by weight of cholesteryl carbamate having as the substituent group at the nitrogen atom of the carbamate a substituted hydrocarbon group, and from about 40 to about 90% by weight of cholesteric liquid crystal;
said substituted hydrocarbon group being selected from the group consisting of a 2-(2-methoxyethoxy) ethyl group, 2-(2-ethoxyethoxy) ethyl group, 2-(2-n-propoxyethoxy) ethyl group, 2-(2-n-butoxyethoxy) ethyl group, ricinoleyl group, anisyl group, phenetyl group, p-chlorophenyl group, and a p-nitrophenyl group, said cholesteric liquid crystal being taken from the group consisting of cholesteryl halides, cholesteryl ethers, cholesteryl esters, cholesteryl carbonates, cholesteryl thiocarbonates, 24-methylcycloaltonol esters, 24, 28-dihydrocycloeucanol esters and cycloaltenol esters and mixtures thereof.

12. A liquid crystal composition for indicating the occurrence of an electric field which consists essentially of from about 10 to about 60% by weight of cholesteryl carbamate having as the substituent group at the nitrogen atom of the carbamate a substituted hydrocarbon group, and from about 40 to about 90% by weight of cholesteric liquid crystal;
said substituted hydrocarbon group being selected from the group consisting of substituted aliphatic groups having a chemical formula such that one methylene group in the alpha position is diminished from a 2-(2-methoxyethoxy) ethyl group, 2-(2-ethoxyethoxy) ethyl group, 2-(2-n-propoxyethoxy) ethyl group, 2-(2-n-butoxyethoxy) ethyl group and a ricinoleyl group, said cholesteric liquid crystal being taken from the group consisting of cholesteryl halides, cholesteryl ethers, cholesteryl esters, cholesteryl carbonates, cholesteryl thiocarbonates, 24-methylcycloaltonol esters, 24,28-dihydrocycloeucanol esters and cycloaltenol esters and mixtures thereof.

13. A method for indicating the occurrence of an electric field including the steps:
a. employing a cholesteryl liquid crystal composition consisting essentially of from about 10 to about 60% by weight of a cholesteryl carbamate having, as the substituent group at the nitrogen atom of the carbamate a member selected from the group consisting of a phenyl group, a monocyclic aromatic hydrocarbon group having a linear aliphatic hydrocarbon group of not more than 8 carbon atoms, and a substituted hydrocarbon group, and from about 40 to about 90% by weight of cholesteric liquid crystal taken from the group consisting of cholesteryl halides, cholesteryl ethers, cholesteryl esters, cholesteryl carbonates, cholesteryl thiocarbonates, 24-methylcycloaltonol esters, 24, 28-dihydrocycloeucanol esters and cycloaltenol esters and mixtures thereof, said substituted hydrocarbon group being selected from the group consisting of a 2-(2-methoxyethoxy) ethyl group, 2-(2-ethoxyethoxy) ethyl group, 2-(2-n-propoxyethoxy) ethyl group, 2-(2-n-butoxyethoxy) ethyl group, ricinoleyl group, groups of the above listed chemical formulae diminished by a methylene group in the alpha position thereof, an anisyl group, phenetyl group, p-chlorophenyl group, and a p-nitrophenyl group; and
b. applying an electric voltage across the cholesteric liquid crystal composition and effecting a clear color change therein.

* * * * *

UNITED STATES PATENT AND TRADEMARK OFFICE
CERTIFICATE OF CORRECTION

PATENT NO. : 3,975,287
DATED : August 17, 1976
INVENTOR(S) : MASAHIKO SAGANE

It is certified that error appears in the above-identified patent and that said Letters Patent are hereby corrected as shown below:

Column 1, line 33, change "fo" to --for--;

Column 3, line 1, change "group" tp --groups--;

Column 3, line 49, after "that" insert --it--;

Column 5, line 19, after "green." delete "The";

Column 5, line 20, begin new paragraph with --The voltage was applied continuously, with some breaks for--;

Column 5, line 26, before "particular" insert --no--;

Signed and Sealed this

Twelfth Day of April 1977

[SEAL]

Attest:

RUTH C. MASON
*Attesting Officer*

C. MARSHALL DANN
*Commissioner of Patents and Trademarks*